United States Patent [19]

Byrne et al.

[11] Patent Number: 5,093,338
[45] Date of Patent: Mar. 3, 1992

[54] LIPOPHILIC MACROLIDE USEFUL AS AN IMMUNOSUPPRESSANT

[75] Inventors: Kevin Byrne, W. Trenton; Robert T. Goegelman, Linden; Otto Hensens, Red Bank, all of N.J.; Louis Kaplan, New City, N.Y.; Jerrold M. Liesch, Princeton Junction, N.J.

[73] Assignee: Merck & Co., Inc., Rahway, N.J.

[21] Appl. No.: 690,410

[22] Filed: Apr. 23, 1991

[51] Int. Cl.$^5$ .................. A61K 31/395; C07D 491/16
[52] U.S. Cl. ................................ 514/291; 540/456; 540/452
[58] Field of Search ............... 540/546, 542; 514/291, 514/63

[56] References Cited
U.S. PATENT DOCUMENTS 5,023,262  6/1991  Caufield et al. .................... 514/291
5,023,263  6/1991  Von Borg ............................ 514/291

Primary Examiner—Robert T. Bond
Attorney, Agent, or Firm—Curtis C. Panzer; Hesna J. Pfeiffer

[57] ABSTRACT

Disclosed is a novel lipophilic macrolide of Formula I:

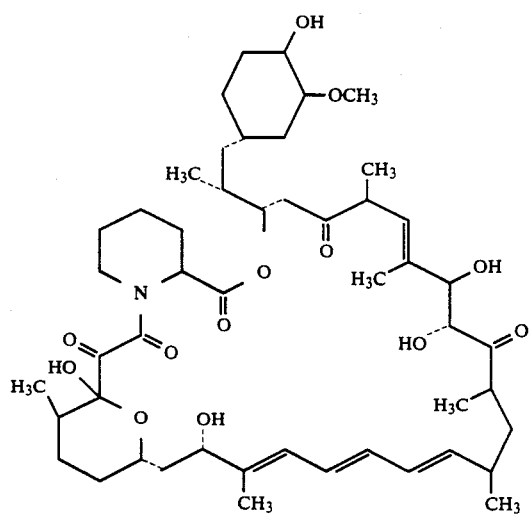

The compound of assigned Formula I is an analog of rapamycin which has activity as an antifungal agent and as an immunosuppressant.

3 Claims, No Drawings

LIPOPHILIC MACROLIDE USEFUL AS AN IMMUNOSUPPRESSANT

BACKGROUND OF THE INVENTION

This invention relates to compounds having activity as an antifungal agent and as an immunosuppressant.

In particular, this invention relates to analogs of the compound rapamycin, which is a compound of the following formula:

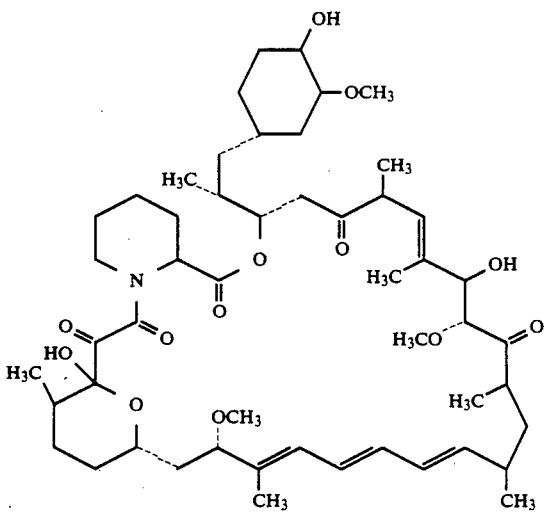

which is useful as an antifungal agent and is useful in the suppression of the immune response.

As early as 1975, rapamycin was identified as an antifungal antibiotic harvested from a Streptomyces hygroscopicus culture, which culture was isolated from an Easter Island soil sample. See Vezina et al., J. Antibiot. 28, 721-726 (1975); and U.S. Pat. No. 3,929,992, which issued to Sehgal, et. al. Dec. 30, 1975. The ability of this compound to inhibit the immune response was first described by Martel, R. et al., Can. J. Physiol. Pharmacol., 55, 48-51 (1977). In this work, the authors show the utility of this compound in inhibiting the response to allergic encephalomyelitis, adjuvant-induced arthritis and antibody production in rats. More recently, Calne, R. Y. et al., has shown rapamycin to be immunosuppressive in rats given heterotopic heart allografts. Calne, R. Y. et al., Lancet vol. 2, p. 227 (1989). Equally important, less toxicity was experienced than would be anticipated with FK-506 (U.S. Pat. No. 4,894,366, assigned to Fujisawa, which issued on Jan. 16, 1990), with which rapamycin shares some structural features.

More recently, rapamycin has been shown to be useful in combination therapy with Cyclosporin A. This combination has the advantage of reducing the amount of Cyclosporin A required to produce its immunosupressive effect, such as in heart, kidney, bowel, pancreas or other transplantation, and thereby effectively reducing the nephrotoxicity inherent in treatment with Cyclosporin A. See Stepkowski, S. M. et al., Transplantation Proceedings, vol. 23, pp 507-508 (1991).

As appreciated by those of skill in the art, and as exemplified by Harding, M. W. et al., Nature, vol. 341, p. 758-760 (1989) and Devlin, J. P. and Hargrave, K. D. Tetrahedron, vol. 45, p. 4327-4369 (1989), Cyclosporin A, FK-506, rapamycin, and analogs thereof, can be expected to share a broad range of utilities as immunosuppressive agents. Cyclosporin A, FK-506, rapamycin and analogs thereof find utility in the prevention of rejection or organ and bone marrow transplants; and in the treatment of psoriasis, and a number of autoimmune disorders such as type 1 diabetes mellitus, multiple sclerosis, autoimmune uveitis, and rheumatoid arthritis. Additional indications are discussed infra.

SUMMARY OF THE INVENTION

This invention relates to a compound assigned of Formula I:

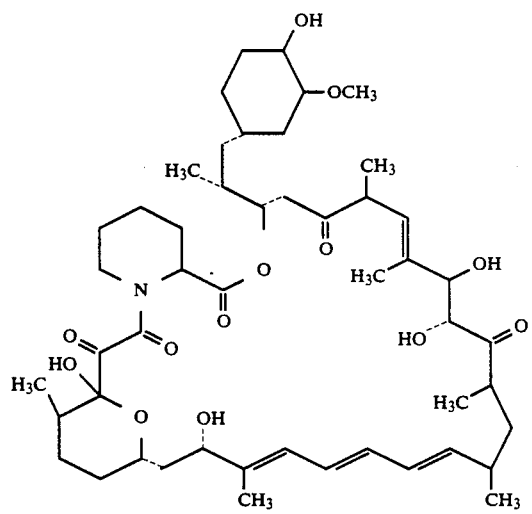

which compound is an analog of rapamycin and which compound is an antifungal agent and a useful immunosuppressant.

DETAILED DESCRIPTION OF THE INVENTION

This invention relates to a compound of assigned Formula I,

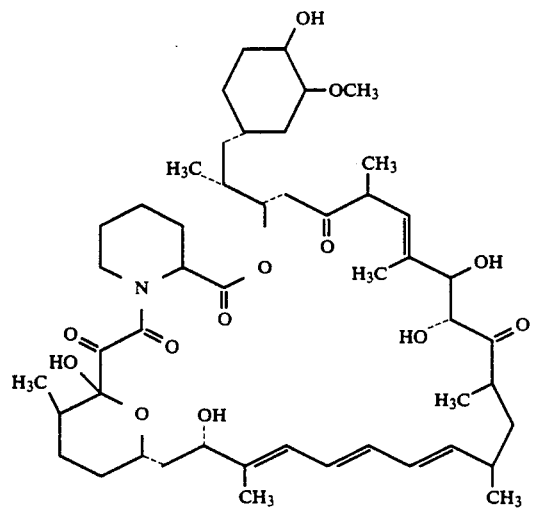

The compound of Formula I may also be described as 7,29-bisdesmethyl rapamycin. The invention also relates to substantially pure compound of Formula I. For purposes of this specification substantially pure shall designate a purity in excess of 98% and free of rapamycin.

This invention also relates to pharmaceutical compositions for inducing immunosuppresion in a subject in need of such treatment, comprising: administration of a therapeutically effective amount of 7,29-bisdesmethyl rapamycin.

In view of its immunosuppressive activity, 7,29-desmethyl rapamycin is useful for the prophylaxis and treatment of diseases and conditions requiring a reduction of the immune response. Thus they may be used to suppress the proliferation of lymphocytes and immunocytes, e.g. in treatment of autoimmune diseases or in preventing the rejection of transplants e.g. skin, lung, heart, heart-lung, bone-marrow, kidney, spleen and corneal transplants.

Specific auto-immune diseases for which the compound of formula I are useful include all of those for which treatment with cyclosporin and/or FK-506 has been proposed or used, for example, aplastic anaemia, pure red cell anaemia, isopathic thrombocytopaenia, systemic lupus erythematosus, polychondritis, scleroderma, Wegener granulomatosis, chronic active hepatitis, myasthenia gravis, psoriasis, Steven-Johnston syndrome, idiopathic sprue, Crohn's disease, Graves opthalmopathy, sarcoidosis, multiple sclerosis, primary biliary cirrhosis, primary juvenile diabetes, uveitis posterior, interstitial lung fibrosis and psoriatic arthritis as well as insulin-dependent diabetes mellitus, nephrotic syndrome and AIDS.

This invention also relates to a pharmaceutical compositions for inducing immunosuppression in a subject in need of such treatment, comprising a therapeutically effective amount of Cyclosporin A and 7,29-bisdesmethyl rapamycin.

This invention also relates to a method of inducing immunosuppresion in a subject in need of such treatment, comprising administration of a therapeutically effective amount of 7,29-bisdesmethyl rapamycin.

The compound of Formula I can be conveniently prepared by fermentation of a culture of *Streptomyces hygroscopicus* such as NRRL 5491, which strain can be obtained from the culture collection at the National Center for Agricultural Utilization Research, USDA, ARS, Peoria Ill. NRRL 5491 is also available from the American Type Culture Collection, Rockville, Md. as ATCC 29253. This organism, and procedures for standard cultivation are described in Vezina et al., J. Antibiot. 28, 721-726 (1975); Sehgal et al J. Antibiot. 28, 727-732, and U.S. Pat. No. 3,929,992; said references being hereby incorporated by reference.

As appreciated by those of skill in the art, microorganisms for production of 7,29-bisdesmethyl rapamycin may include other natural or artificial mutants or variants derived from the described culture. The artificial production of mutant strains may be achieved by physical or chemical mutagens, for example, ultraviolet irradiation or N-nitrosoguanidine treatment and the like. Recombinant DNA techniques such as protoplast fusion, plasmid incorporation, gene transfer and the like are also envisioned.

In general production of 7,29-bisdesmethyl rapamycin can be achieved by cultivation of NRRL 5491 in the presence of sinefugin by conventional aerobic fermentation of suitable nutrient media which contain sources of assimilable carbon, nitrogen and inorganic salts. Sinefungin concentration may range from 0.1 to 5.0 mM; preferably 1.0 mM.

In general, many carbohydrates such as glucose, maltose, mannose, sucrose, starch, glycerin, millet jelly, molasses, soy bean and the like can be used as sources of assimilable carbon. Sources of assimilable nitrogen includes such materials as yeast and casein hydrolysates, primary yeast, yeast extracts, cottonseed flour, soybean solids, wheat germ, meat extracts, peptone, corn steep liquor, and ammonium salts. The inorganic salt nutrients which can be incorporated in the culture medium are the customary salts yielding sodium, iron, magnesium, potassium, cobalt, phosphate and the like. In general, of course, the techniques employed will be chosen having regard to industrial efficiency. The nutrient media described herein are merely illustrative of the wide variety of media that may be employed and are not intended to be limiting.

The fermentation has been carried out at temperatures ranging from about 20° to 32° C.; however, for optimum results it is preferable to conduct the fermentation at about 27° C. The pH of the medium is controlled at about pH 6-7 by the use of suitable organic or inorganic buffers incorporated into the fermentation medium or by the periodic addition of a base such as sodium hydroxide. Good yields of 7,29-bisdesmethyl rapamycin can be achieved within 30 to 96 hours. Variation of the medium or the microorganism will alter the yield of the compound of 7,29-bisdesmethyl rapamycin and/or its rate of production. The preferred media compositions are set forth in the examples. The terms "seed" and "production media" are employed as terms of the art. Generally, a seed medium supports rapid growth of the microorganism and a small portion thereof (seed) is used to inoculate a production medium for large scale fermentation.

Specific examples of fermentation isolation and recovery conditions we have found to be advantageous are provided in the Examples Section below.

As stated above, in view of its immuno-suppressive activity, 7,29-bisdesmethyl rapamycin is useful for the prophylaxis and treatment of diseases and conditions requiring a reduction of the immune response. Thus they may be used to suppress the proliferation of lymphocytes and immunocytes, e.g. in treatment of autoimmune diseases or in preventing the rejection of transplants e.g. skin, lung, heart, heart-lung, bone-marrow, kidney, spleen and corneal transplants.

Specific auto-immune diseases for which the compound of formula I are useful include all of those for which treatment with cyclosporin and FK 506 has been proposed or used, for example, aplastic anaemia, pure red cell anaemia, isopathic thrombocytopaenia, systemic lupus erythematosus, polychondritis, scleroderma, Wegener granulomatosis, chronic active hepatitis, myasthenia gravis, psoriasis, Steven-Johnston syndrome, idiopathic sprue, Crohn's disease, Graves opthalmopathy, sarcoidosis, multiple sclerosis, primary biliary cirrhosis, primary juvenile diabetes, uveitis posterior, interstitial lung fibrosis and psoriatic arthritis as well as insulin-dependent diabetes mellitus, nephrotic syndrome and AIDS.

For all these uses the dosage will, of course, vary depending on the compound employed, mode of administration and treatment desired. However, in general, satisfactory results are obtained when administered at a daily dosage of from about 1 mg to about 200 mg per kg animal body weight, conveniently given in divided doses 2 to 4 times a day or in sustained release form. For the larger mammals, the total daily dosage is in the range from about 50 to about 5000 mg, and dosage forms suitable for oral mg (e.g. 25–300 mg) of the compounds admixed with a solid or liquid pharmaceutical carrier or diluent.

The present invention also provides a pharmaceutical composition comprising a compound of formula I such as in association with a pharmaceutical carrier or diluent.

Such compositions may be in the form of, for example, a solution, a tablet or a capsule and in ointments especially for the treatment of psoriasis.

7,29-bisdesmethyl rapamycin may be administered by any conventional route, in particular in accordance with means currently practiced in relation to administration of cyclosporin, in particular via intravenous infusion, e.g. in the case of organ transplant, pre- and immediately post-transplant, as well as during episodes of gastrointestinal disturbance which might otherwise impair absorption, or orally, e.g. in the form of an oral solution.

Biological activity as a immunosuppressant can be measured in terms of inhibition of interleukin-2 production, and inhibition of T-cell proliferation (The utility of the invention can also be shown by its ability to inhibit various fungus). Results are provided in the Examples section.

T-cell proliferation was measured in mouse T-cell cultures stimulated with ionomycin plus phorbol myristate acetate (PMA). (This assay is described in detail in Dumont, F. J. et al, J. Immunol. (1990) 144:251.) Spleen cell suspensions from C57B1/6 mice were prepared and separated on nylon wool columns. The recovered T-cells were suspended at $10^6$ cells/ml in complete culture medium with addition of ionomycin (250 ng/ml) and PMA (10 ng/ml). The cell suspension was immediately distributed in 96 well-flat bottom microculture plates at 200 μl/well. Control medium or various concentrations of test compound were added in triplicate wells at 20 μl/well. Parallel cultures were set up with exogenous IL-2 (50 units/ml). The plates were incubated at 37° C. in a humidified atmosphere of 5% $CO_2$-95% air for 44 hours. The cultures were then pulsed with tritiated-thymidine (2 uCi/well) for an additional 4 hour period and cells were collected on fiber glass filters using a multisample harvester. Incorporated radioactivity was measured in a BETAPLATE COUNTER (Pharmacia/LKB, Piscataway, NJ) and the mean count per minute (cpm) values of triplicate samples calculated. The percent inhibition of proliferation was calculated according to the formula:

$$\% \text{ Inhib.} = 100 - \frac{\text{mean cpm experimental}}{\text{mean cpm control medium}} \times 100$$

The following examples illustrate the preparation of this compound and, as such, are not to be construed as limiting the invention set forth in the claims appended hereto.

EXAMPLE 1

Production of 7,29-Bisdesmethyl Rapamysin

The producing culture for production of rapamycin was NRRL 5941, which is also known as ATCC #29253. Seed cultures were started from either a well sporulated slant of the culture grown on Bennetts agar medium consisting of 0.1% yeast extract, 0.1% beef extract, 0.2% N-Z AMINE A and 1.0% glucose, or 100 ul of $3 \times 10^9$ spores preserved in 10% glycerol and stored at $-79°$ C. Seed medium A consisted of:

| Component | g/L |
| --- | --- |
| $KNO_3$ | 2.0 |
| Glucose | 20.0 |
| Yeast Extract | 20.0 |
| HYCASE SF[1] | 20.0 |
| $FeSO_4 \cdot 7H_2O$ | 0.025 |
| NaCl (12.5%) | 4.0 ml |
| $MgSO_4 \cdot 7H_2O$ (12.5%) | 4.0 ml |
| $MnSO_4 \cdot H_2O$ (0.5%) | 1.0 ml |
| $ZnSO_4 \cdot 7H_2O$ (1.0%) | 1.0 ml |
| $CaCl_2 \cdot 2H_2O$ (2.0%) | 1.0 ml |
| PH was adjusted to 7.0 before sterilization. | |

[1]HYCASE SF is a product of SHEFFIELD PRODUCTS, Norwich, N.Y.

Seed incubations were conducted with 44 ml of medium in a 250 ml baffled erylenmeyer flask and, after inoculation as stated above, incubated at 27° C. and 220 RPM for 48 to 72 hours.

Production flasks were inoculated with 1.0 to 1.5 ml of seed culture, tube fermentations inoculated with 0.1 ml, into production medium RAP-21 consisting of:

| Component | g/L |
| --- | --- |
| Glucose | 20.0 |
| Glycerol | 20.0 |
| $(NH_4)_2SO_4$ | 5.0 |
| $KH_2PO_4$ | 2.5 |
| $K_2HPO_4$ | 2.5 |
| L-Lysine | 4.0 |
| NUTRISOY[1] | 30.0 |
| Morpholinoethanesulfonic acid (MES) | 21.3 |
| PH was adjusted to 6.3 before sterilization. | |

[1]NUTRISOY is a product of ARCHER DANIELS, Midland, Michigan.

Production incubations were carried out with 30 to 44 ml of medium in a 250 ml non-baffled erylenmeyer flask or 3.0 ml in a $25 \times 150$ mm tube shaking at 220 RPM at 25° C. At 43 to 48 hours a sterile solution of sinefungin was added to the flask so that the final concentration of sinefungin was between 0.1 and 1.0 mM, and the fermentation continued for an additional 24 to 48 hours.

The fermentation was harvested and the fermentation broth extracted with an equal volume of MeOH. After shaking for 30 minutes, the extract was centrifuged and the supernatant analyzed by high performance liquid chromatography (HPLC).

HPLC analysis consisted of:

Solvent composition 1: WATERS 510 pumps (WATERS ASSOCIATES, Milford, Mass.) delivering a mobile phase composed of MeOH/Water (76:24) at 1.0 ml/min.

Composition 2: Gradient conditions with an initial composition of acetonitrile/$H_2O$ (60:40) maintained for 5.0 minutes, and then changing to acetonitrile/$H_2O$ (75:25) in a linear fashion over a 20 minute time interval. The final composition was maintained for 10 minutes before the column was re-equilibrated at the initial conditions.

Composition DESRAP: a gradient solvent run with initial conditions of MeOH/0.1% $H_3PO_4$ (68:32) changing to a ratio of (83:17) in a linear fashion over 30 minutes before re-equilibration to initial conditions.

Column: WHATMAN PARTISIL 5 ODS-3 $4.0 \times 250$ mm, operated at room temperature.

Detector: WATERS Model 490 variable wavelength detector and a WATERS Model 990 Photodiode array detector. Optimal wavelength for detection was 277 nm.

Injection of 20 ul of methanol extract of the sinefungin treated fermentation produced a chromatogram obtained using the DESRAP solvent conditions with 7.29 bisdesmethyl rapamycin having an $R_t$ of 16.3 minutes in comparison to rapamycin at 24.6.

EXAMPLE 2

The procedure used in this production of desmethyl analogues is modeled after that described above. A spore stock was used which had been frozen in 0.01% TWEEN 80 (polyethylenesorbitan,) and 10% glycerol. A 0.1 ml aliquot was used to inoculate a seed flask containing 50 ml of seed medium A. The flask was incubated at 27° C. at 220 rpm for 43 hours. Aliquots of 1.0 and 0.1 ml of seed was used to inoculate production flasks containing 34 ml RAP-21, medium, or 25×150 mm tubes containing 3.4 ml RAP-21, respectively. Production tubes and flasks were incubated at 26° C. and 240 rpm. At 32 hours, sinefungin was added to the flasks and tubes such that the final concentration in duplicate flasks was 0.0, 0.5 or 1.0 mM, while that in triplicate tubes was 0.0, 0.25, 0.50, 0.75, or 1.00 mM sinefungin. Flasks and tubes were harvested at 56 hours, and extracted using an equal volume of MeOH and shaken for 30 minutes.

Analysis of the products was accomplished using either a WHATMEN PARTISIL C8 or a WHATMAN PARISIL 5 ODS-3 HPLC column operated at 60 C, and run with a mobile phase of acetonitrile/0.1% $H_3PO_4$ operating at 1.0 ml/minute and starting at a ratio of 50/50 and changing to 65/35 in a linear fashion over 20 minutes. Monochromatic detection was carried out at 277 nm and the UV/visible spectra of selected peaks were determined using the WATERS 990 photodiode array detector. The invention had an $R_t$ of 18.0 minutes in comparsion to rapamycin at 33.5 minutes.

A partial purification of the control and treated fermentations was accomplished using adsorption onto a C-18 SEP-PAK (WATERS ASSOCIATES) cartridge followed by selective elution of the compounds of interest. The procedure consisted of passing 3.0 ml of fermentation broth that had been extracted with MeOH/H2O (1:1) through an activated SEP-PAK cartridge, and then sequentially eluting the compounds of interest first with MeOH/H2O of either (75:25) or (8:2) and then pure MeOH. This procedure eliminated most of the very polar materials and served to enrich two of the most polar rapamycin analogues away from some compounds with similar retention times. Elution of the SEP-PAK with MeOH/H2O (8:2) afforded material enriched in the invention.

A complete isolation procedure used preliminary to obtaining Mass Spectroscopic identification is as follows:

Step A

Nine hundred ml. of whole broth was filtered using a SUPER-CEL precoat. The mycelia cake was slurried with four hundred ml. of acetone and stirred with good agitation for two hours. The mixture was filtered and the mycelia cake discarded. The acetone filtrate was concentrated to a 50 ml aqueous concentrate and extracted with 3×50 ml of ethyl acetate. The extracts were combined and dried with sodium sulfate. The dried extract was concentrated to dryness.

Step B

The product of step A was taken up in 2.5 ml of ethyl acetate. The solution was chromatographed on 250 ml of E. MERCK silica-gel (0.04 to 0.06 mm) previously equilibrated with ethyl acetate. Chromatograpgy was carried out with ethyl acetate at 8 ml/min collecting a 100 ml forecut followed by one hundred 8 ml fractions. Ninty-eight 8 ml fractions were collected. The solvent was then switched to 97/2.5 v/v ethyl acetate/methanol and ninty-eight 8 ml fractions were collected. The solvent was then switched to 95/5 v/v eth acetate/methanol collecting four 250 ml fractions. Fractions 66 through 198 were combined on the basis of HPLC analysis. A 10% aliquot of the combined fractions was then concentrated to dryness.

Step C

The product of step B was taken up in 75 mcl of methanol and chromatographed on WHATMAN PARTISIL 10 ODS-3 column 0.94×50 cm. at room temperature using a solvent system of 67/33 v/v methanol/water at a flow rate of 4.5 ml./minute. The effluent stream was monitored at 277 nm collecting fractions based on the U.V. trace. Fractions two and three, retention time forty-nine minutes, were combined and concentrated to dryness to yield 1.0 milligrams of the compound of Formula I.

FAB-MS

This material was found to have a molecular weight of 885 as determined by FAB-MS (observed in the lithium spiked spectrum (M+Li) at m/z 892). The EI spectrum exhibits characteristics ions at m/z 175, and 304.

Biological Activity

The biological activity of the rapamycin analogue was assessed by fractionating concentrated eluants from SEP-PAK purification of the sinfungin treated and untreated fermentation extracts. The fractions were neutralized by addition of 50 ul of 0.25M MES per ml eluant, dried on a lyophilizer, and evaluated for antifungal activity in the antifungal assay (AFA), and immunosuppressive activity by a modified version of the T-cell proliferation assay. AFA results are given below in Table 1.

TABLE 1

Antifungal Activity of Sinefungin Induced Rapamycin Fermentation Products

| Peak Fraction | Peak Rt (Min) | Zone Size (mm) | | | | |
|---|---|---|---|---|---|---|
| | | A. niger | Penicillium sp. | Ustilago zeae | Candida tropical | Candida albicans |
| 1S-17[a] | 17 | 0 | 0 | 0 | 11 | 0 |
| 2S-32[a] | 32 | 34 | 34 | 25 | 28 | 23 |
| 4S-32[b] | 32 | 27 | 23 | 17 | 27 | 18 |
| 5S-17[b] | 17 | 28 | 27 | 20 | 23 | 18 |

[a]untreated
[b]treated

This data indicates that for samples not treated with sinefungin, there is no antifungal activity associated with the 17 minute region of the HPLC chromatograms. However, there is activity associated with the same region in samples that had been treated with sinefungin and the activity was similar in profile to the rapamycin eluted in region 32.

Samples sent for T cell proliferation assay were fractionated in 1.0 minute fractions through the region of interest. The same samples eluted from the SEP-PAKs mentioned above for AFA analysis were also used for the T cell proliferation analysis. The 1.0 ml, 1.0 minute fractions were each neutralized with 50 ul of 0.25M MES, pH 7.3 and evaporated to dryness. In performing the T cell assay the samples were redissolved in 100 ul MeOH at dilutions of 1/100, 1/500, 1/2500 and 1/12500. Samples are considered to be positive in the assay when they give an inhibition level of 50% or greater. The peak at 17-18 minutes was eluted from the SEP-PAK with 80% MeOH. A fractionation of the region for untreated control eluted with 80% methanol was done in addition to the sinefungin treated samples. The T cell proliferation data is summarized in Table 2.

TABLE 2

T-Cell Proliferation Activity of Sinefungin Treated Rapamycin Fermentation

| SAMPLE | DILUTION HAVING ACTIVITY | (FRAC. NUMBER) ACTIVITY [1] | | | |
|---|---|---|---|---|---|
| | | (16) | (17) | (18) | (19) |
| Control[2] | 1/100 | 10 | 33 | 33 | 10 |
| Product | 1/2500 | 1 | 64 | 74 | 18 |

[1] only % INHIBITION values greater than 50% are considered active.
[2] no sinfungin in fermentation This table shows that the new peak seen in the 17-18 minute region possesses T-cell proliferation inhibitory activity even diluted out 1 to 2500. The control fractions did not show any activity greater than 50% inhibition even at the highest concentration tested.

What is claimed is:

1. A compound of assigned Formula I, which compound is 7,29-desmethyl rapamycin

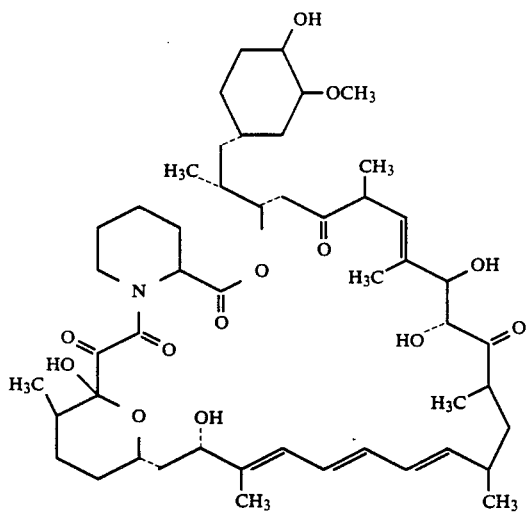

or a pharmaceutically acceptable salt thereof.

2. A pharmaceutical compositions for inducing immunosuppression in a subject in need of such treatment, comprising:
   a non-toxic therapeutically effective amount of compound according to claim 1 and a pharmaceutically acceptable carrier.

3. A method of inducing immunosuppression in a subject in need of such treatment comprising:
   administration to said subject a non-toxic therapeutically effective amount of compound according to claim 1.

* * * * *